US005840755A

United States Patent [19]

Liedtke

[11] Patent Number: 5,840,755
[45] Date of Patent: Nov. 24, 1998

[54] METHOD AND COMPOSITION FOR TOPICAL THERAPY OF HEADACHES

[75] Inventor: Rainer K. Liedtke, Munich, Germany

[73] Assignee: American Pharmed Labs, Inc., New York, N.Y.

[21] Appl. No.: 682,351

[22] Filed: Jul. 17, 1996

[30]    Foreign Application Priority Data

Jul. 17, 1995 [DE]  Germany .................. 195 26 019.8

[51] Int. Cl.$^6$ ................................. A01N 37/12
[52] U.S. Cl. .................... 514/535; 514/626; 514/627
[58] Field of Search ...................... 514/535, 626, 514/627

[56]    References Cited

U.S. PATENT DOCUMENTS 5,008,289  4/1991  Bernstein ................... 514/535

Primary Examiner—Terressa M. Mosley
Attorney, Agent, or Firm—Oblon, Spivak, McClelland, Maier & Neustadt, P.C.

[57]    ABSTRACT

A composition for topical therapy of headaches, which contains a topical carrier system for intact mammalian skin of forehead or temples or both, which contains a therapeutically effective dose of a local anesthetic for delivery to a skin surface underneath the topical carrier system.

14 Claims, No Drawings

METHOD AND COMPOSITION FOR TOPICAL THERAPY OF HEADACHES

BACKGROUND OF THE INVENTION

1. Field of the Invention

The present invention relates to a method and composition for topical therapy of headaches.

2. Description of the Background

It is known that headache symptoms which occur as attacks primarily have neurological and vascular causes, however, psychosomatic stress factors, physical environmental factors, functional or organic spinal column disorders related to stress, stimulation of certain cerebral nerves, and even the abuse of substances such as alcohol, nicotine, and analgesics are also implicated.

These symptoms are presently treated to a great extent with pharmaceuticals, such as systemically active, nonopiate, oral or injectable analgesics and antiphlogistics, partially in combination with psychosomatic or physical therapy. Other treatment methods, such as acupuncture, have also been used in combination with these treatments, acupuncture.

However, the conventional pharmacotherapies as a whole still do not afford sufficiently tolerable and effective forms of treatment. In particular, derivatives of salicylic acid, preferably acetylsalicylic acid, nonsteroidal antiphologics, for example, ibuprofen, or aniline derivatives, for example, paracetamol, are used as the pharmacologically active principle (e.g., K. Brune, W. Beck in: M. Zenz, I. Jura (Editors) Lehrbuch der Scherztherapie (Manual of Pain Therapy), WFG, Stuttgart, 1993, pp. 121–135). For migraines, ergotamine derivatives, different tranquilizers of the benzodiazepine group, are used in addition, as well as β-blockers for prophylaxis.

Unfortunately, all systemic headache therapies presently in use have in common a considerable number of side effects. For example, salicylic acid derivatives and nonsteroidal antiphlogistics are associated with considerable gastric disorders as a consequence of the antiproliferative active mechanism. Paracetamol is associated with metabolic stress of the liver and kidney functions, especially in prolonged use and with higher doses. The ergotamine derivatives are associated particularly with a very high incidence of gastrointestinal feelings of nausea. The application of these systemic therapies, therefore, is limited by the spectrum in each case of the product-specific, undesirable effects, since systemic interventions involve all organs and organ systems.

A more effective pharmacological principle might be a suitable form of the application of low-dosed local anesthetics. Amide group- and ester group-containing local anesthetics, for example, lidocaine as an amide group-containing local anesthetic, exhibit inhibition of the rapid sodium ion influx into nerve fibers, as a pharmacological activity mechanism. In this way, they block the impulse conduction of the nerve path which, in principle, involves all regional nerve fibers. The sensory and anatomically thinner fibers are more sensitive than the motoric fibers, due to their morphology (G. R. Strichartz (Editor), Local Anesthetics, Handbook of Experimental Pharmacology, Vol. 81, Springer, Berlin—New York, 1987). The activity effects can also be differentiated in this way.

A systemic application of local anesthetics might be possible, invasively, by means of injections. However, this option is practically eliminated due to the danger of systemic overdose with, among others, serious cardiac side effects. Direct application of local anesthetics through local injection to the head is technically possible and may be performed in different ways. However, local injections are not only painful, but, moreover, they can never be done directly by the patient. For example, the local surface injection technique involves the so-called neural therapy with trigger points (J. T. Travell, D. G. Simons, Myofascial Pain and Dysfunction, Vol. I/II, Williams & Wilkins, Baltimore, 1983) and requires experienced, medical handling and technique. Therefore, it is limited to use in clinically severe disorders. Further, the use of conventional topical formulations, for example, creams, among other things, does not afford either exact dosage or positioning. Moreover, such formulations do not afford continuous penetration over a prolonged period of application.

Thus, a need exists for a method and composition for topical therapy of headaches, which overcome the above disadvantages.

SUMMARY OF THE INVENTION

Accordingly, it is an object of the present invention to provide a composition for topical therapy of headaches.

It is also an object of the present invention to provide a method for topical therapy of headaches.

Accordingly, the above objects and others are provided by a composition for topical therapy of headaches, which contains a topical carrier system for application to intact skin of a mammalian forehead or temples or both and a local anesthetic for delivery to a region of skin underneath the topical carrier system.

DETAILED DESCRIPTION OF THE PREFERRED EMBODIMENTS

In accordance with the present invention, a composition is provided for topical therapy of headaches, which contains a topical carrier system for intact mammalian skin of forehead or temples or both, which contains a therapeutically effective dose of a local anesthetic for delivery underneath the topical carrier system.

Although the method and composition of the present invention may be used with any mammal, such as horses, cows, dogs and cats, for example, it is particularly advantageous to use the present invention in conjunction with humans.

In order to improve the efficacy and tolerability of the topical therapy, in one embodiment of the invention, amide group- or ester group-containing local anesthetics are contained in concentration ranges of about 0.5–40% by wt. based upon the total weight of the composition.

In accordance with the present invention, any local anesthetic having amide or ester groups may be used. Such local anesthetics are well known as are synthetic methodologies for preparing the same. For example, lidocaine, tetracaine, bupivacaine, prilocaine, mepivacaine, etidocaine, procaine and benzocaine may be mentioned. However, any amide group- and/or ester group-containing local anesthetic may be used either alone or in combination with others. Other such local anesthetics are, for example, the esters propoxycaine, hydroxyprocaine, chloroprocaine, ambucaine, metabutoxycaine, proparacaine, paraethoxycaine, butacaine, isobucaine, hexylcaine, piridocaine, piperocaine and cyclomethycaine; or the amides procainamide, dibucaine, pyrrocaine and tolycaine. All of these compounds are known with synthetic methodologies for preparing the same being described in *Organic Chemistry of Drug Synthesis*, Lednicer et al (Wiley, 1977).

In order to improve the efficacy and tolerability of the therapy, in another embodiment of the invention, two or more local anesthetics with different pharmacokinetics are combined in the topical carrier system used, and these individual substances are present in concentrations such that the total concentration of the two or more active ingredients is not more than 40% by wt. based on the total weight of the composition.

In order to make the therapy more safe and easier to use, in a further embodiment of the invention, the topical carrier system is present in forms which correspond to the special characteristics of the field of application of the skin of the forehead and/or temples of the patient. The external shape of the topical carrier system is, for example, round, oval, rectangular, with concave or convex outer shapes, or the carrier system also can be segmented by the user into appropriate shapes, with or without additional aides.

One particular advantage which can be achieved with the present invention arises from the fact that a noninvasive and local treatment option for symptoms of headache is presented for the first time with this topical carrier system described herein.

Further, topical therapy with local anesthetics in the present topical carrier system makes possible a locally targeted and prolonged therapeutically effective treatment of the terminal and functionally interlinked nerve paths in the area of the head.

Since this area also has good cutaneous absorption capacity, topical doses which are very low can also be used. Systemic danger, as is present with customary oral or injectable analgesics and antiphlogistics, is thereby avoided, because the local anesthetics, for example, lidocaine, are metabolized to a large extent in the delayed cutaneous absorption, so that no systemic activity levels appear with corresponding organ stresses.

The therapy can be managed and maintained with low doses, and as needed, can be interrupted by removal of the carrier.

Generally, although conventional dosages of local anesthetics may be used, it is preferred that the therapeutically effective topical amount of local anesthetic in the carrier, be for lidocaine, for example, in the range of about 10 mg to 50 mg for delivery to the intact skin over a span of about 12 to 36 hours, at a rate in the range of about 0.05 to 1 mg/cm$^2$ per hour.

Therefore, the topical therapy of headaches, in accordance with the present invention, has no systemic side effects such as systemic analgesic or antiphlogistic therapies, because a prior active ingredient distribution through the entire body which stresses the other organs and organ systems is avoided. In addition, local anesthetics also exhibit good local tissue tolerability.

As examples of technically suitable designs of a topical carrier system for the skin of the forehead and temples which may be used with local anesthetics in accordance with the present invention, the descriptions of the technical carrier systems in U.S. Pat. No. 4,765,986, EP 0,205,974, DE P3716575.5-45, and DE P3811564.6-45 are cited, without, however, limiting the invention in any way to these described techniques. U.S. Pat. No. 4,765,986 is incorporated herein in the entirety by reference.

Additionally, since the topical carrier system is in a form suitable for the forehead and/or temples, the external shape of the topical carrier system is round, oval, rectangular or semicircular, with concave or convex external shapes. Alternatively, the carrier system can be segmented by the user into appropriate shapes, with or without additional aids.

Having now fully described the invention, it will be apparent to one of ordinary skill in the art that many changes and modifications can be made to the above-described embodiments without departing from the spirit and the scope of the present invention.

What is claimed as new and desired to be secured by Letters Patent of the United States is:

1. A topical carrier system for topical therapy of headaches for application to intact mammalian forehead or temple skin or both, which comprises a therapeutically effective amount or dose of a local anaesthetic for delivery from said topical carrier system to said mammalian forehead or temple skin or both, wherein said topical carrier system comprises at least one component having around, oral, rectangular or semicircular shape.

2. A method for topical therapy of headaches, which comprises applying a therapeutically effective amount of a local anesthetic from a topical carrier system attached on forehead or temple skin or both of a mammal in need thereof, wherein said topical carrier system comprises at least component having a one round, oval, rectangular or semicircular shape.

3. The topical carrier system of claim 1, wherein said local anaesthetic is an amide group- or ester group-containing local anesthetic.

4. The topical carrier system of claim 1, wherein two or more local anesthetics are used each having different pharmacokinetics.

5. The topical carrier system of claim 1, wherein said local anaesthetic is used in an amount of about 0.5 to 40% by weight based upon the total weight of the composition.

6. The topical carrier system of claim 1, wherein said local anesthetic is selected from the group consisting of lidocaine, tetracaine, prilocaine, bupivacaine, mepivacaine, etidocaine, procaine and benzocaine.

7. The topical carrier system of claim 1, wherein said local anesthetic is lidocaine.

8. The topical carrier system of claim 1, wherein the therapeutically effective amount or dose of local anesthetic used is about 10 mg to 50 mg.

9. The method of claim 2, wherein said local anesthetic is an amide group- or ester group-containing local anesthetic.

10. The method of claim 2, wherein two or more local anesthetics are used, each having different pharmacokinetics.

11. The method of claim 10, wherein said local anaesthetic is used in an amount of 0.5 to 40% by weight based upon the total weight of the composition.

12. The method of claim 2, wherein said mammal is human.

13. The method of claim 2, wherein the local anesthetic used is lidocaine.

14. The method of claim 13, wherein the local anesthetic is used in an amount of 10 mg to 50 mg.

* * * * *